United States Patent [19]

Hanna et al.

[11] Patent Number: 5,879,668
[45] Date of Patent: Mar. 9, 1999

[54] TRANSFER-RESISTANT MAKE-UP COMPOSITIONS AND PROCESS OF MAKING

[75] Inventors: Fifi Hanna, Kearny, N.J.; Michael D. Swanborough, Baltimore, Md.

[73] Assignee: L'Oreal, Paris, France

[21] Appl. No.: 794,005

[22] Filed: Feb. 3, 1997

[51] Int. Cl.$^6$ ............................... A61K 7/032; A61K 7/04
[52] U.S. Cl. .......................... 424/70.7; 424/61; 424/63; 424/64; 424/70.1; 424/401; 514/844
[58] Field of Search ................... 424/401, 61, 63, 424/64, 70.1, 70.7; 514/844

[56] References Cited

U.S. PATENT DOCUMENTS

| 5,356,617 | 10/1994 | Schlossman | 424/63 |
| 5,505,937 | 4/1996 | Castrogiovanni et al. | 424/64 |
| 5,523,091 | 6/1996 | Pastour et al. | 424/401 |

*Primary Examiner*—Jyothsna Venkat
*Attorney, Agent, or Firm*—Oblon, Spivak, McClelland, Maier & Neustadt, P.C.

[57] ABSTRACT

A cosmetic composition having waterproof, long wear and transfer resistance properties based on a water-in-oil emulsion.

20 Claims, No Drawings

TRANSFER-RESISTANT MAKE-UP COMPOSITIONS AND PROCESS OF MAKING

FIELD OF INVENTION

The prevent invention relates to waterproof, long wear cosmetic products which have transfer resistant properties. Processes for making invention cosmetic products also make up part of the present invention. The base vehicle of the invention cosmetic products is a water-in-oil emulsion wherein the oil is principally based upon $C_{10}$–$C_{14}$ linear or branched hydrocarbons.

BACKGROUND OF THE INVENTION

Transfer resistant and long wear cosmetic products provide several benefits currently desired by cosmetic consumers. Cosmetics having long wear properties avoid the necessity of frequent reapplication, and transfer resistance avoids unwanted smudging, staining, etc., both for the wearer and for those coming into contact with the wearer. Such cosmetics thus are highly desirable due to their excellent properties and enjoy high consumer demand.

OBJECTS OF THE INVENTION

It is one object of the present invention to provide a cosmetic product which is waterproof.

It is another object of the present invention to provide a cosmetic product which has long wear properties.

It is another object of the present invention to provide a cosmetic product which has transfer resistant properties.

It is another object of the present invention to provide cosmetic products having one or more of the above-identified objects and which may be used as a liquid foundation, a concealer, a mascara, an eyeliner, a blush, etc.

It is another object of the present invention to provide W/O emulsion cosmetic product which contains no silicone oil such as volatile silicones.

It is another object of the present invention to provide processes for making cosmetic products which meet one or more of the above objects at, below or above room temperature.

These and other objects will become apparent to those of ordinary skill in the cosmetic arts upon a further appreciation of the invention, a summary of which follows.

SUMMARY OF THE INVENTION

The present invention cosmetic product is a water-in-oil (W/O) emulsion in which water (the disperse phase) is emulsified in oil (the continuous phase). The oil is preferably a $C_{10}$–$C_{14}$ saturated, linear or branched, hydrocarbon, more preferably a $C_{11}$–$C_{13}$ saturated, linear or branched, hydrocarbon, more preferably a branched $C_{12}$ saturated hydrocarbon such as isododecane. Of course, mixtures of these hydrocarbons may be used and often are provided by commercial "technical" grades of these hydrocarbons.

The invention W/O emulsion contains solid particles, preferably pigment particles and possibly other types of particles, which may be coated with a hydrophobic coating to increase affinity to the skin. Coating is particularly preferred for pigment particles contained in the invention W/O emulsion. Red, yellow and black iron oxide pigment particles and titanium dioxide particles are particularly preferably coated with a hydrophobic coating.

In addition to particles, the invention W/O emulsion preferably contains at least two different types of surfactants, one being an a "oil surfactant" having a hydrophobic-lipophobic balance (HLB) of from 3–4.5, the other being a "water surfactant" having an HLB of 5.5–7.5.

Finally, the invention W/O emulsion preferably contains a water-soluble and/or water-dispersable polymer, such as a water-soluble polyurethane, or water-dispersable latex, to act as a film former, and also preferably contains a gelator, optionally with an activator, to gel the oil phase. Of course, and as discussed more fully below, the invention W/O emulsion may also contain various ingredients common in the cosmetics art such as moisturizers, light diffusers, fillers, salts (electrolytes), emulsifiers preservatives, fragrances, etc.

While not bound by any theory, the inventors believe that the present invention cosmetic product provides its beneficial properties (i.e., waterproof, long wear, transfer resistant, etc.) through a fixative system wherein the water-soluble latex, gelator and hydrophobicly coated pigment act in concert to provide excellent adhesion to the skin, hair, eyelashes, lips, etc.

DETAILED DESCRIPTION OF THE PREFERRED EMBODIMENTS

Throughout the present application the term "percent by weight" or the symbol "wt. %" means percent by weight based on total weight of cosmetic composition unless specifically stated otherwise. Names of particular ingredients refer to Cosmetic Toiletry and Fragrance Association (CTFA) names. Volumes 1 and 2 of the International Cosmetic Ingredient Dictionary, $6^{th}$ Edition, 1995, published by the CTFA are incorporated herein by reference as is Milady's Skin Care and Cosmetic Ingredients Dictionary, Milday's Publishing Company, Albany, N.Y., 1994 and Volume 8 of the Kirk-Othmer Encyclopedia of Chemical Technology, pp. 900–930 (emulsions).

The invention W/O emulsion preferably contains from 20–55 wt. % water, more preferably 30–50 wt. %, most preferably 37–45 wt % water, including 25, 30, 35, 36, 37, 38, 39, 40, 41, 42, 43, 44, and 45 wt. % water, and all values, ranges and subranges between all given values. The particular water used is not limited, and may be distilled and/or deionized water, etc., and may be obtained from any source including so-called natural sources such as springs, etc., known or having a reputation as providing water which is beneficial to the health and/or beauty of the user. The hardness, softness, etc., of the water used in the invention W/O emulsion is not limited and is preferably selected to provide a stable emulsion.

The pH of the water phase of the present invention W/O emulsion preferably falls within the range of from 2–10 (all ranges in this application include end points), more preferably 4–8, most preferably 5–7.5 and may be adjusted according to art-known procedures using acid, base, buffer, etc. Water may be used as received in the present invention, or may first have its pH adjusted before incorporation into an invention emulsion. If water-soluble agents are to be added to the present invention emulsion which are pH-sensitive, the pH of the invention component can be adjusted accordingly to a pH of, e.g., 2, 3, 3.5, 4, 4.5, 5, 5.5, 6, 6.5, 7, 7.5, 8, 8.5, 9, 9.5, 10, etc.

The present invention W/O emulsion preferably contains 10–55, preferably 15–30, more preferably 20–28 including 21, 22, 23, 24, 25, 26 and 27 wt. % oil including all values, subranges and ranges between all given values. The oil preferably is a hydrocarbon-based oil, more preferably containing one or more $C_{10}$–$C_{14}$ saturated hydrocarbons. While some unsaturation may be tolerable in the invention oil, the most preferred oils useful herein are linear and branched $C_{10}$–$C_{14}$ alkanes having the formula $C_nH_{2n+2}$. Naturally, useful alkanes according to the present invention are $C_{10}$, $C_{11}$, $C_{12}$, $C_{13}$ and $C_{14}$ alkanes, more preferable alkanes being $C_{11}$–$C_{13}$ alkanes, the most preferred being $C_{12}$ alkanes, particularly branched $C_{12}$ alkanes.

The branched alkanes useful in the present invention may be branched at as many or as few available branch points as possible. For example, the branches themselves may have one or as many as possible carbons, and may themselves be branched. Methyl, ethyl, propyl, butyl, pentyl, hexyl, etc. branches thus are possible as are isopropyl, isobutyl, 2-methyl propyl-, etc. branches. A particularly preferred oil is isododecane (CTFA). Isomeric $C_{12}H_{24}$ compounds such as the methylundecanes, dimethyldecanes, trimethylnonanes, tetramethyloctanes, etc. are also useful herein.

One, two or three conjugated or non-conjugated double bonds may be present in invention oils. General formulae of $C_nH_{2n}$ and $C_nH_{2n-2}$ and $C_nH_{2n-4}$ thus are possible for invention oils. The oils of these latter formulae may be or may include cyclic structures, with or without unsaturation, although this is not as preferred as the linear and branched oils.

The alkanes used as oils herein include those provided as "technical" mixtures by commercial suppliers, which typically are mixtures of linear and variously branched alkanes of the formula $C_nH_{n+2}$. Of course, the present invention oil may contain a mixture of any of the above-described oils useful herein.

The present invention oil may contain, in addition to the hydrocarbon oils described above, other oils commonly used in W/O cosmetic emulsions such as silicone oils, including volatile silicone oils such as linear and cyclic silicone oils, etc. For certain applications and in certain situations, based on the desired feel and behavior of the composition, cosmetic products containing 50–100 wt. %, including 60, 70, 80 and 90 wt. % and all values, subranges and ranges between all given values, of the hydrocarbon oils described above, based on total weight of oil, are preferred, however. The absence of silicone oils such as volatile silicone oils in the invention oil is another preferred embodiment.

The present invention W/O emulsion preferably contains 1–20 wt. %, including 2, 4, 6, 8, 10, 12, 14, 16, and 18 wt. % and all values, ranges and subranges between all given values, of solid particles (powders) including both pigment particles and other particles. The size of the particles (powders) is not limited and may be from, e.g., 0.001–200 microns, including 0.01, 0.1, 1, 5, 10, 20, 50, 100 and 150 microns and all values, ranges and subranges between all given values. Red, yellow and black iron oxide particles, titanium dioxide particles, zinc oxide particles, zinc stearate particles, and boron nitride particles are preferred examples of particles which may be used herein. Other powders useful herein include pearl pigments such as alumina, barium sulfate, mica, calcium carbonate, zirconium oxide, iron titinate, ultramarine blue, prussian blue, chromium oxide, chromium hydroxide, cobalt oxide, cobalt titinate, titanium dioxide coated mica and colored non-white inorganic particles consisting of metal salts which are insoluble in the cosmetic medium and useable in cosmetics, referenced in the Color Index under section "Inorganic Coloring Matters" and which bear the numbers 77000 to 77947. The white pigments included in this list are also useful herein. See U.S. Pat. No. 5,496,543, incorporated herein by reference.

In the highly preferred embodiments, the invention W/O emulsion contains pigment particles including one or more of the iron oxide particles and titanium dioxide particles described above, and in a most preferred embodiment of the present invention the W/O emulsion contains pigment particles which have been coated so as to render them generally hydrophobic.

While it is possible that all particles contained within the invention W/O emulsion can be coated with a hydrophobic coating, it is particularly preferred that pigment particles, such as red, black or yellow iron oxide and titanium dioxide, be coated with a hydrophobic coating so as to, it is thought, improve their adhesion to the skin, increase their long-wear properties, and improve transfer resistance. Coatings useful for rendering the particles of the invention, preferably the pigment particles of the invention, hydrophobic include amino acid salts such as aluminum acyl glutamate, polyethylene, lecithin and collagen. See U.S. Pat. No. 5,523,091, incorporated herein by reference.

Invention coatings may either be adsorbed onto and/or absorbed into the solid particles of the invention by solvent evaporation, milling, etc. or chemically bound thereto through reaction of, e.g., a pigment surface OH group and a reactive group on the coating compound. Preferably the coated particles are hydrophobic, which can be determined by their behavior in water (dispersed or suspended) and the coating amount varied accordingly.

The present invention W/O emulsions preferably contain one or more surfactants to stabilize the emulsion. Most preferably, two different types of surfactants are used, one an "oil" surfactant and one a "water" surfactant, the oil surfactant having an HLB of from 3–4.5, preferably 3.5–4.2, more preferably 3.7–4 and most preferably 3.8–3.9, including all values, subranges and ranges between all given values, the water surfactant having an HLB of 5.5–7.5, preferably 5.8–7.2, more preferably 6–7 including 6.2, 6.4, 6.6 and 6.8, and all values, subranges and ranges between all given values. HLB values are given in the literature for surfactants and, if not, may be calculated by art-known methods such as by the formula given in column 3 of U.S. Pat. No. 5,015,469, incorporated herein by reference.

Examples of the oil surfactant include dimethicone copolyol, laurlymethicone copolyol, glyceryl stearate, beeswax, cetyl dimethicone copolyol, polyglyceryl-4 isosterate, hexyl laurate, etc. Of course, mixtures of useful oil surfactants may be used.

Preferred water surfactants include polysorbate 20 (TWEEN 20), Carbowax 200, PEG 4, Carbowax 1450, etc. Mixtures may be used.

Other suitable oil and water surfactants useful in the present invention include those meeting the above HLB constraints described in U.S. Pat. Nos. 4,311,695 (Dow), 4,782,095 (Union Carbide), 4,698,178 (Goldschmidt), and 4,122,029 (Dow), all incorporated herein by reference, as well as those disclosed in McCutcheon's, *Detergents and Emulsifiers*, North American edition (1986), published by Allured Publishing Corporation and McCutcheon's *Functional Materials*, North American edition (1992), both incorporated herein by reference. Other non-limiting examples of suitable surfactants for use in the compositions of the present invention include those meeting the invention HLB constraints listed in the following U.S. Pat. Nos.: 5,151,210, 5,151,209, 5,120,532, 5,011,681, 4,788,006, 4,741,885, 4,704,272, 4,557,853, 4,421,769, and 3,755,560, all incorporated herein by reference.

The amount of oil surfactant useful in the present invention W/O emulsion is from 5–15 wt. %, more preferably 6–14 wt. %, most preferably 8–10 wt. %. The amount of water surfactant useful herein is from 0.1–10 wt. %, more preferably 1–3 wt. %, most preferably 0.4–0.8 wt. %.

The present invention further preferably comprises, within the W/O emulsion, a water-soluble or water-disperable polymer such as a polyurethane, particularly polycarbamyl polyglycol ester, or ammonium acrylate copolymer, sodium polymethylacrylate, etc. It is thought that these polymers act as film-formers. Of course, mixtures of such polymers may be used. The amount of water-soluble and/or water-dispersable polymer useful herein ranges from 0.1–10 wt. %, preferably 0.5–5 wt. %, more preferably 1–2 wt. %. Further examples of useful water-soluble and water-dispersable polymers are found in U.S. Pat. Nos. 3,927,199, 4,946,932, 5,266,322, 5,288,493 and PCT WO 96/33689, all incorporated herein by reference.

Useful polymers herein also include anionic, cationic, nonionic or amphoteric polyurethanes, acrylic polyurethanes, polyvinylpyrrolidone polyurethanes, polyester polyurethanes, polyether polyurethanes, polyureas, polyurea/polyurethanes and mixtures thereof.

The polyurethane may be, for example, a polyurethane copolymer, polyurea/urethane or polyurea, which is aliphatic, cycloaliphatic or aromatic, comprising, by itself or as a mixture;

at least one block originating from linear or branched aliphatic and/or cycloaliphatic and/or aromatic polyether, and/or at least one block originating from aliphatic and/or cycloaliphatic and/or aromatic polyether, and/or at least one silicone-containing block, substituted or otherwise, branched or otherwise, for example polydimethylsiloxane or polymethylphenylsiloxane, and/or at least one block comprising fluorine-containing groups.

The polyurethanes as defined in the invention may also be obtained from polyesters, branched or otherwise, or from alkyds comprising mobile hydrogens which are modified by reaction with a diisocyanate and a difunctional (for example dihydro-, diamino-, or hydroxyamino-) organic compound, additionally comprising either a carboxylic acid or carboxylate group or a sulphonic acid or sulphonate group, or else a neutralizable tertiary amine group or a quaternary ammonium group.

The present invention W/O emulsion preferably comprises a gelator and, more preferably, a gelator and a gelator activator. Clays are particularly preferred oil gelators useful herein, such as Quaterinum-18 Bentonite, Bentones (e.g., Bentone 27, 34,38), hectorites, etc. Propylene carbonate is a particularly preferred activator for this gelator. Low carbon number (1–10) linear and branched alcohols are also useful activators herein. Other oil gelling agents (gelators) useful herein include condensates of p-benzaldehyde and penta and higher hydric alcohols such as those described in the paragraph bridging columns 5 and 6 of U.S. Pat. No. 5,362,482, incorporated herein by reference. The amount of gelator useful herein typically is from 0.1–10 wt. %, more preferably 0.5–5 wt. %, more preferably 1–2 wt. %. Gelator activator may be present in amounts of from 0.001–5 wt. %, more preferably 0.01–1 wt. %. Mixtures of gelators and mixtures of gelator activators may be used.

The present invention cosmetic product preferably contains, as additional ingredients, one or more of a moisturizer, light diffuser, filler, electrolyte, emulsifier and preservative. Moisturizers are generally well known in the cosmetic art and include, in particular, propylene glycol. Glycols are also used to provide a plasticizer effect herein. Moisturizers may be used in any convenient amount to provide moisturizing effects, including 0.1–10 wt. %.

Light diffusers useful herein include plastic particles having preferred diameters of from 5–20 micrometers such as nylon-12 particles. Such light diffusers hide fine lines and provide excellent feel. The light diffuser may be present in amounts of from 0.1–10 wt. %, although the amount is not limited.

Fillers useful herein include talc and other fillers known in the cosmetic art. The filler of the present invention is useful for providing a relatively consistent solids content and for providing body to the composition. Useful amounts of filler include 0.1–10 wt. %.

The emulsion of the present invention preferably has dissolved therein, in the aqueous phase, electrolytes which help balance the emulsion system and provide stability. Common salts such as sodium chloride, magnesium sulfate, etc. are useful for this purpose, and are known in the art. Bases such as sodium hydroxide may also be used. Amounts of electrolytes useful herein typically range from 0.1–10 wt. %.

Emulsifiers also help to stabilize the invention composition. Examples are triethanolamine, ammonium hydroxide, etc. Useful amounts include 0.01–10 wt. %.

The final preferred ingredient of the present invention is a preservative which provides stability, etc. Any known preservative useful in the cosmetic art may be used herein in amounts of from, e.g., 0.01–10 wt. %. Examples of useful preservatives include methylparben, diazolidinyl urea and butylparaben.

The present invention cosmetic product may contain additional components not specifically described above, including those materials described at column 16, line 25-column 19, line 12 of U.S. Pat. No. 5,585,104, incorporated herein by reference. Retinoic acid, alpha-hydroxy acids, ascorbic acid, Vitamin E and sunscreens are particularly preferred additional components useful herein.

The present invention W/O emulsions may be prepared by any methodology known in the art. See, in particular, *Emulsions and Emulsion Technology*, Part I, Ed. Kenneth J. Lissant, Marcel, Decker, Inc., New York (1974), incorporated herein by reference. The invention emulsion preferably comprises droplets of from 1000 to 0.001 microns, more preferably 0.1 to 100 microns including 1, 10, 20, 40, 50, 60, 80 and 90 microns, all values, subranges, and ranges between all given values. The size is not limited. One benefit of the present invention W/O emulsions is that they may be made at, below, or above room temperature with mixers and homogenizers well known in the art. In a preferred embodiment, the pigment phase typically is milled and coated, mixed with other non-water ingredients, and water is added thereto with mixing and homogenizing as necessary.

The invention emulsion can vary in consistency from a liquid to a paste to a solid depending upon water amount, etc.

The components of the invention emulsion are commercially available and/or within the skill of an ordinary artisan to produce.

EXAMPLE

The present invention will now be described by reference to a non-limiting example. The product brochures and MSD sheets corresponding to the materials used in the following Example, and corresponding to those useful components described above, all are incorporated herein by reference.

A make up composition in the form of a liquid is prepared as a W/O emulsion containing the following products:

aluminum acyl glutamate coated iron oxide particles (5 wt. %)

isopropyl titanium triisostearate-coated titanium oxide particles (8 wt. %)

butylparaben (0.1 wt. %)

diazolidinyl urea (0.3 wt. %)

methylparaben (0.2 wt. %)

quaternium-18 bentonite (1.6 wt. %)

talc (1 wt. %)

sodium chloride (0.6 wt. %)

nylon-12 (3 wt. %)

polycarbamyl polyglycol ester (1 wt. %)

surfactant (polyglyceryl-4-isostearate/cetyl dimethicone copolyol/hexyl laurate) (9 wt. %)

isododecane (22 wt. %)

propylene carbonate (0.3 wt. %)

propylene glycol (4 wt. %)

polysorbate 20 (0.2 wt. %)

water qs to 100 wt. %

First, the coated pigment, emulsifiers and oil are mixed and the other solids such as nylon, bentonite, etc. are added thereto and mixed. Separately, the water phase is prepared by mixing the water, latex, etc. The water phase is then added to the oil phase with mixing followed by a high shear mixing to provide an emulsion.

What is claimed is:

1. A water-in-oil emulsion comprising:
    a) water;
    b) isododecane
    c) a first surfactant having an HLB of from 3.5–4.2;
    d) a second surfactant having an HLB of from 6–7;
    e) aluminum acyl glutamate-coated pigment particles;
    f) a water-soluble or water-dispersible polymer; and
    g) an oil gelator, wherein said oil gelator is clay.

2. The emulsion of claim 1, further comprising oil, wherein said oil consists essentially of one or more additional saturated $C_{12}$ branched hydrocarbons.

3. The emulsion of claim 1, further comprising a gelator activator.

4. A method of beautifying the skin, hair, scalp, nails, face, eyelids, eyelashes, mucous membranes or lips comprising the step of applying the emulsion of claim 1 thereto.

5. The emulsion of claim 2, further comprising a gelator activator.

6. A water-in-oil emulsion, consisting essentially of:
    a) water;
    b) isododecane
    c) a first surfactant having an HLB of from 3.5–4.2;
    d) a second surfactant having an HLB of from 6–7;
    e) aluminum acyl glutamate-coated pigment particles;
    f) a water-soluble or water-dispersible polymer; and
    g) an oil gelator, wherein said oil gelator is clay.

7. The emulsion of claim 1, wherein said water-soluble or water-dispersible polymer is water-soluble polyurethane or water-dispersible latex.

8. The emulsion of claim 1, prepared by mixing:
    a) water;
    b) isododecane
    c) a first surfactant having an HLB of from 3.5–4.2;
    d) a second surfactant having an HLB of from 6–7;
    e) aluminum acyl glutamate-coated pigment particles;
    f) a water-soluble or water-dispersible polymer; and
    g) an oil gelator wherein said oil gelator is clay.

9. The emulsion of claim 1, wherein said water has a pH of 4–8.

10. The emulsion of claim 1, wherein said emulsion comprises 15–30 wt. % of said isododecane.

11. A method of beautifying the skin, comprising applying the emulsion of claim 1 thereto.

12. The emulsion of claim 1, wherein said first surfactant has an HLB of from 3.7–4.

13. The emulsion of claim 1, wherein said emulsion comprises 6–14 wt. % of said first surfactant.

14. The emulsion of claim 1, wherein said emulsion comprises 1–3 wt. % of said second surfactant.

15. The emulsion of claim 1, further comprising an alpha-hydroxy acid.

16. The emulsion of claim 1, further comprising a sunscreen.

17. A method of beautifying the lips, comprising applying the emulsion of claim 1 thereto.

18. A method of beautifying the nails, comprising applying the emulsion of claim 1 thereto.

19. A method of beautifying the face, comprising applying the emulsion of claim 1 thereto.

20. A method of beautifying the eyelids, comprising applying the emulsion of claim 1 thereto.

* * * * *